US00PP07965P

United States Patent [19]

Katsuo

[11] Patent Number: Plant 7,965

[45] Date of Patent: Sep. 8, 1992

[54] CRAPE-MYRTLE NAMED SUMMER FLASH

[75] Inventor: Kiyoshi Katsuo, Bunsui, Japan

[73] Assignee: Hokuetsu Nohji Co., Ltd., Niigata, Japan

[21] Appl. No.: 528,353

[22] Filed: May 25, 1990

[51] Int. Cl.[5] ..... A01H 5/00

[52] U.S. Cl. ..... Plt./67.3

[58] Field of Search ..... Plt./54, 54.1, 67.3

*Primary Examiner*—Howard J. Locker

*Attorney, Agent, or Firm*—Oblon, Spivak, McClelland, Maier & Neustadt

[57] ABSTRACT

The subject of the present disclosure is a new and distinct variety of crape-myrtle, named 'Summer Flash', which is characterized by its bright red purple blooms, its dwarf habit, and its extremely heavy branching habit and its extremely numerous amount of blooms. The new variety is hardy and well-branched.

1 Drawing Sheet

BACKGROUND OF THE NEW PLANT

The present invention relates to a new and distinct variety of crape-myrtle, the variety being primarily characterized by bright red purple blooms.

The variety is further characterized by:

From spreading to flat-spreading performance having a (hill spread)/(height) ratio of about 1.6, flat-globe form, dwarf habit (about 40 cm height), extremely heavy branching habit and an extremely numerous amount of blooms.

The new crape-myrtle variety originated in 1985 as a seedling resulting from the crossing of a pair of crape-myrtle plants. The seed parent was 'Summer And Summer', *Lagerstroemia indica L.*, which was bred at a research farm in Uchino-cho, Niigate-shi, Niigate-ken, Japan, and the pollen parent was 'Issai-Sarusuberi', *Lagerstroemia indica L.* This crossing was done at the same research farm as described above in 1984 with the object of producing plants having flowers of different colors from the seed parent, 'Summer And Summer.' The seed parent, 'Summer And Summer' has been registered under No. 1733 on Aug. 18, 1988, under the Japanese Seed and Seedlings Law. The pollen parent, 'Issai-Sarusuberi' is a well-known and popular crape-myrtle plant and is under no protection, such as a patent or plant variety protection certificate. In 1986, the asexual reproduction of this selected seedling was done by me and under my direction at the same research farm as described above by green shoot cutting. Then, observations were made for 2–4 years of grown plants during 1987–1989. The continuous asexual propagation has demonstrated that the novel characteristics would hold true from generation to generation, appear to be firmly fixed, and are transmitted without change through succeeding propagations.

The new crape-myrtle variety differs from its seed parent and pollen parent in the following ways.

| | New Variety Summer Fantasy | Seed Parent Summer And Summer | Pollen Parent Issai-Sarusuberi |
|---|---|---|---|
| Tree-Performance | spreading to flat-spreading | flat-spreading | upright |
| (hill spread)/(tree height) | 1.6 | 3.0 | 0.43 |

-continued

| | New Variety Summer Fantasy | Seed Parent Summer And Summer | Pollen Parent Issai-Sarusuberi |
|---|---|---|---|
| ratio | | | |
| Tree form | flat globe | disc | obovoid |
| Tree height (cm) | dwarf (39.3) | dwarf (20.0) | shrub (130.0) |
| Branching Habit (number of branches on a main trunk) | extremely heavy 18.0 | medium 5.8 | sparse 4.4 |
| Number of inflorescences per one cluster | extremely numerous 17.3 | medium 5.0 | little 3.5 |
| Number of flowers per one inflorescence | extremely numerous 108.0 | medium 32.0 | medium 26.0 |
| Petal color | bright red purple JHS Color Chart 9506 or RHS Colour Chart 63B, 67B, 71C | strong purplish pink JHS Color Chart 9205 or RHS Colour Chart 68A, 68B, 73A | vivid red purple JHS Color Chart 9507 |

The new crape-myrtle variety may be reproduced with ease by stem cuttings. Just after root taking, young shoots come out and spread as growth proceeds. The variety becomes to show from spreading to flat-spreading in tree performance and flat globe in tree form, before appearance of flower buds. The tree height of an adult tree is about 40 cm and the hill spread is about 1.6 times the tree height.

The variety shows extremely heavy branching habit and bears extremely numerous flowers and buds. The blooming period of the variety is long, from July to October in Niigate-shi, Niigate-ken, Japan, and in similar climate elsewhere. The variety also shows a good cold hardiness and can overwinter well without being supported with a pole even in a snowy area.

BRIEF DESCRIPTION OF THE DRAWINGS

The accompanying drawings show typical specimens of the new variety in color as nearly true as is reasonably possible to make the same in color illustrations of this character. In each instance, the photographs were taken at the research farm described above in August, 1989.

DETAILED DESCRIPTION OF THE NEW PLANT

Figure 1:
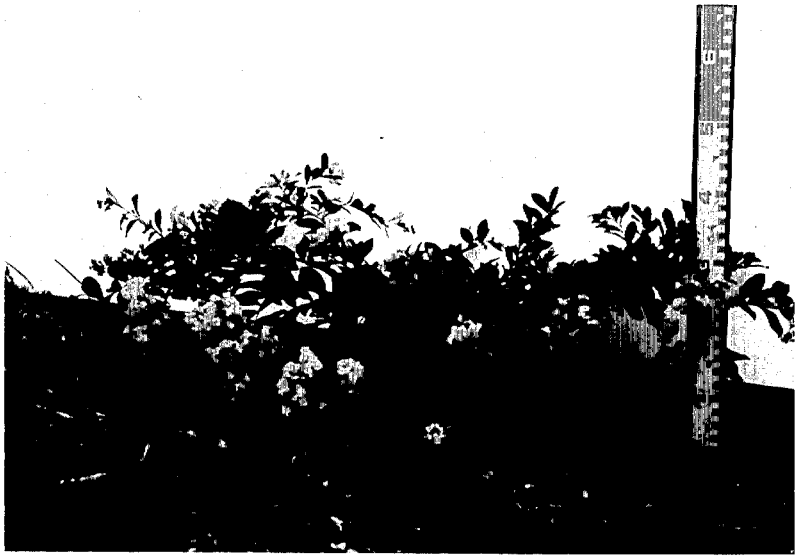
FIG. 1 is a complete view of the new variety together with a scale wherein the dwarf habit of the new variety is apparent.
Figure 2:
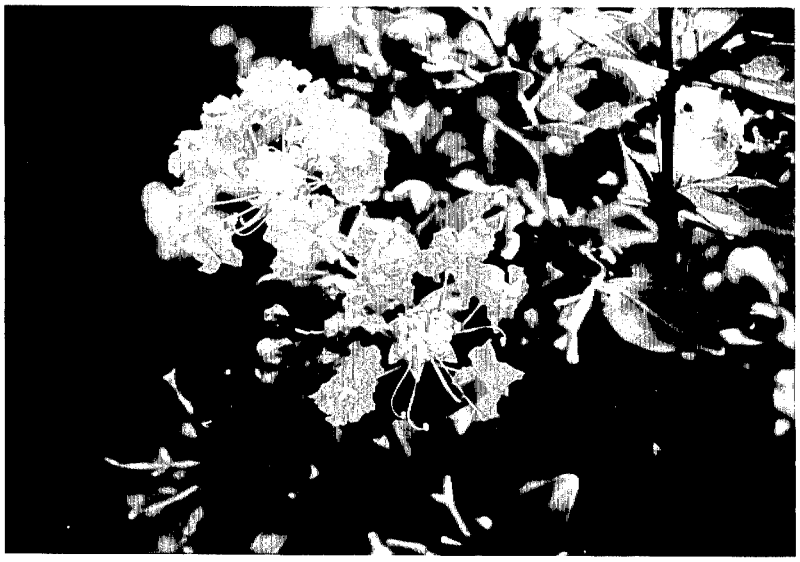
FIG. 2 is a closer view of a blooming peduncle showing the characteristics of the flower, bud and immature fruit.

The following is a detailed description of the characteristics of the new variety as observed at the research farm described above. Color designations are made by reference to JHS Color Chart (Japan Horticultural Scale) or RHS Colour Chart (Royal Horticultural Society) except where common terms of color definition are employed.

Plant:

*Tree performance.*—From spreading to flat-spreading with a (hill spread)/(tree height) ratio of about 1.6.

*Tree form.*—Flat globe.

*Tree height.*—Dwarf, about 35 to 45 cm in adult trees.

Stem:

*Type of trunk.*—Bush.

*Trunk color.*—Purplish brown.

*Young bud.*—Reddish brown in color.

*Branches.*—Color: Reddish brown. Thickness: 4.3 mm (ave. of 50 shoots). Appearance of branch edge: Obvious. Branching habit: Extremely heavy, about 18.0 branches in average on a main trunk. Internode length: Short, about 1 to 2 cm.

Foliage:

*Average leaf length.*—About 5.6 cm.

*Average leaf width.*—About 2.9 cm.

*Leaflets (lamina).*—Broad lanceolate-shaped.

*Top of leaflets.*—acute-shaped (78.3°).

*Base of leaflets.*—acute-shaped.

*Margin.*—Entire.

*Wave of leaflets.*—None.

*Thickness of leaflets.*—0.4 mm (ave. of 50 leaflets)

*Color of immature leaflets.*—Vivid yellow green (JHS Color Chart 3506).

*Color of mature leaflets.*—Upper side is dark green (JHS Color Chart 3716) or RHS Colour Chart 137A, 137B, 148B, under side is dull yellow green (JHS Color Chart 3514) or RHS Colour Chart 146B, 147B, 148B.

*Mottling.*—None.

*Color change.*—Red.

*Luster.*—Weakly-glossy finish.

*Hair.*—None on both the upper surface and the under surface.

*Petiole.*—Pale green in color. Length: 1.0 to 1.1 mm.

Flower:

*Bud.*—Trapezoidal

*Cluster.*—Cone-shaped, upward, broad and long.

*Inflorescence.*—Extremely numerous, 17.3 on average per one cluster.

*Semiinflorescence.*—5 to 10 per the lowest inflorescence.

*Number of flowers.*—108.0 on average per one inflorescence.

*Shape or form.*—Single, six petals.

*Fragrance.*—Present, slight.

*Pedicel.*—4.5 to 5.5 mm.

*Appearance of calyx tube edge.*—Developed.

Petals:

*Color.*—Overall bright red purple (JHS Color Chart 9506) or RHS Colour Chart 63B, 67B, 71C with no variation and slight fading in tone.

Shape.—Orbiculate with strong wave.

*Petal base.*—Bright red purple (JHS Color Chart 9506) or RHS Colour Chart 63B, 67B, 71C) in color and the length of the claw is 8 to 9 mm.

Reproductive organs:

*Style.*—Strong red.

*Pistil.*—One.

*Filaments.*—Pale red.

*Anthers.*—Yellow.

*Stamens.*—30 to 35 arranged around the pistil.

Fruit:

*Shape.*—Ellipsoid, 10 mm in length (ave. of 50 fruits) and 8.3 mm in width (ave. 50 fruits, being rotundate on the base and top.

*Color.*—Green in immaturity, and changes to dark purple in maturity.

Growth:

*Habit.*—Dwarf, 35 to 45 cm height.

*First foliage appears.*—April.

*Blooming term.*—July to October.

*Days for bearing flowers.*—About 100.

*Defoliation.*—November.

*Cole hardiness.*—High.

*Heat tolerance.*—High.

*Disease resistance.*—High.

*Pest resistance.*—High.

Species designation: 'Summer Flash' is designated as *Lagerstroemia indica L.* hybrid.

The present new variety can survive at a temperature as low as −15° C. and is resistant to *Cercospora lythracearum* Heald et Wolf, generally known as leaf blight.

The following additional descriptive botanical information is also provided:

Bloom diameter: 4.6 to 5.4 cm.

Petal size (width): 1.5 to 1.8 cm.

Persistence of individual blooms: One day from blooming. On the second day after blooming, the flower color begins to fade gradually.

Fertile seeds: Are observed.

(i) *Seed color.*—dark-grayish brown (JHS Colour Chart 1619) or (RHS Colour Chart 200C).

(ii) *Samara.*—seed winged at the top.

(iii) *Seed size.*—Length: 6.4 mm. (avg. of 50 seeds). Width: 2.9 mm (avg. of 50 seeds).

(iv) li Number of seeds per fruit.—24 (avg. of 50 fruits).

Tree width: 62.9 cm. (avg. of 50 plants).

As will be apparent to those skilled in horticultural science, the new variety as herein described may vary in slight detail due to climate, soil and cultural conditions under which the variety may be grown and the stage of growth.

What is claimed as new and desired to be secured by Letters Patent of the United State is:

1. A new and distinct variety of crape-myrtle plant, substantially as herein described and illustrated.

* * * * *